(12) United States Patent
Bucay-Couto (10) Patent No.: US 8,920,826 B2
(45) Date of Patent: *Dec. 30, 2014

(54) MEDICAL IMAGING REFERENCE DEVICES

(75) Inventor: Weenna Bucay-Couto, Burlington, MA (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 2043 days.

This patent is subject to a terminal disclaimer.

(21) Appl. No.: 11/326,995

(22) Filed: Jan. 6, 2006

(65) Prior Publication Data

US 2006/0171895 A1    Aug. 3, 2006

Related U.S. Application Data

(63) Continuation-in-part of application No. 10/209,476, filed on Jul. 31, 2002, now Pat. No. 8,685,427.

(51) Int. Cl.
| | | |
|---|---|---|
| A61F 13/00 | (2006.01) | |
| A61L 31/18 | (2006.01) | |
| A61K 9/00 | (2006.01) | |
| A61F 2/07 | (2013.01) | |
| A61M 31/00 | (2006.01) | |
| A61B 19/00 | (2006.01) | |
| A61F 2/06 | (2013.01) | |
| A61F 2/04 | (2013.01) | |

(52) U.S. Cl.
CPC .............. *A61B 19/54* (2013.01); *A61L 31/18* (2013.01); *A61B 2019/5454* (2013.01); *A61F 2250/0067* (2013.01); *A61K 9/0024* (2013.01); *A61F 2/06* (2013.01); *A61B 2019/5433* (2013.01); *A61F 2/07* (2013.01); *A61F 2/04* (2013.01); *A61M 31/002* (2013.01); *A61B 2019/5437* (2013.01)
USPC ........................................ 424/422

(58) Field of Classification Search
None
See application file for complete search history.

(56) References Cited

U.S. PATENT DOCUMENTS

| | | | |
|---|---|---|---|
| 3,279,996 A | 10/1966 | Long, Jr. et al. | |
| 3,618,604 A | 11/1971 | Ness | |
| 3,832,252 A | 8/1974 | Higuchi et al. | |
| 3,845,770 A | 11/1974 | Theeuwes et al. | |
| 3,854,480 A | 12/1974 | Zaffaroni | |
| 3,916,899 A | 11/1975 | Theeuwes et al. | |

(Continued)

FOREIGN PATENT DOCUMENTS

| | | |
|---|---|---|
| DE | 33 47 660 A1 | 7/1985 |
| DE | 101 50 995 A1 | 4/2003 |

(Continued)

OTHER PUBLICATIONS

Boze, Broox, "Diagnostic Imaging Agents" Southern Methodist University, PowerPoint presentation, Nov. 15, 2004, Faculty.smu.edu/jbuynak/PowerPoint.ppt.

(Continued)

*Primary Examiner* — Carlos Azpuru
*Assistant Examiner* — Casey Hagopian
(74) *Attorney, Agent, or Firm* — Bookoff McAndrews, PLLC (57) ABSTRACT

A medical device can be placed within or on the body of a patient. The device can include one or more imaging agents to allow visualization of the location of the device by an imaging system such as an MRI, an ultrasound, a PET, a CT, or an IR imaging system.

21 Claims, 6 Drawing Sheets

(56) References Cited

U.S. PATENT DOCUMENTS

| | | |
|---|---|---|
| 3,948,254 A | 4/1976 | Zaffaroni |
| 3,993,072 A | 11/1976 | Zaffaroni |
| 4,036,227 A | 7/1977 | Zaffaroni |
| 4,054,139 A | 10/1977 | Crossley |
| 4,069,307 A | 1/1978 | Higuchi et al. |
| 4,111,202 A | 9/1978 | Theeuwes |
| 4,186,745 A | 2/1980 | Lewis et al. |
| 4,240,163 A | 12/1980 | Galin |
| 4,286,590 A | 9/1981 | Murase |
| 4,309,996 A | 1/1982 | Theeuwes |
| 4,391,797 A | 7/1983 | Folkman et al. |
| 4,472,327 A | 9/1984 | Neefe |
| 4,589,880 A | 5/1986 | Dunn et al. |
| 4,603,152 A | 7/1986 | Laurin et al. |
| 4,657,024 A | 4/1987 | Coneys |
| 4,723,950 A | 2/1988 | Lee |
| 4,816,264 A | 3/1989 | Phillips et al. |
| 4,853,978 A | 8/1989 | Stockum |
| 4,902,503 A | 2/1990 | Umemura et al. |
| 4,923,450 A | 5/1990 | Maeda et al. |
| 4,933,178 A | 6/1990 | Capelli |
| 4,946,899 A | 8/1990 | Kennedy et al. |
| 4,957,479 A | 9/1990 | Roemer |
| 4,959,217 A | 9/1990 | Sanders et al. |
| 4,973,304 A | 11/1990 | Graham et al. |
| 4,978,391 A | 12/1990 | Jones |
| 5,080,892 A | 1/1992 | Yamamori et al. |
| 5,091,205 A | 2/1992 | Fan |
| 5,091,442 A | 2/1992 | Milner |
| 5,098,379 A | 3/1992 | Conway et al. |
| 5,102,401 A | 4/1992 | Lambert et al. |
| 5,102,402 A | 4/1992 | Dror et al. |
| 5,114,719 A | 5/1992 | Sabel et al. |
| 5,130,159 A | 7/1992 | Shlenker et al. |
| 5,135,516 A | 8/1992 | Sahatjian et al. |
| 5,137,671 A | 8/1992 | Conway et al. |
| 5,165,952 A | 11/1992 | Solomon et al. |
| 5,171,318 A | 12/1992 | Gibson et al. |
| 5,178,870 A | 1/1993 | Schaeken et al. |
| 5,217,493 A | 6/1993 | Rad et al. |
| 5,261,896 A | 11/1993 | Conway et al. |
| 5,272,012 A | 12/1993 | Opolski |
| 5,279,594 A | 1/1994 | Jackson |
| 5,282,784 A | 2/1994 | Willard |
| 5,304,121 A | 4/1994 | Sahatjian |
| 5,316,774 A | 5/1994 | Eury et al. |
| 5,328,954 A | 7/1994 | Sarangapani |
| 5,344,411 A | 9/1994 | Domb et al. |
| 5,360,415 A | 11/1994 | Yabushita et al. |
| 5,362,754 A | 11/1994 | Raad et al. |
| 5,366,505 A | 11/1994 | Farber |
| 5,370,681 A | 12/1994 | Herweck et al. |
| 5,372,600 A | 12/1994 | Beyar et al. |
| 5,378,475 A | 1/1995 | Smith et al. |
| 5,389,314 A | 2/1995 | Wang |
| 5,409,012 A | 4/1995 | Sahatjian |
| 5,462,644 A | 10/1995 | Woodson |
| 5,468,787 A | 11/1995 | Braden et al. |
| 5,509,900 A | 4/1996 | Kirkman |
| 5,512,055 A | 4/1996 | Domb et al. |
| 5,527,337 A | 6/1996 | Stack et al. |
| 5,554,147 A | 9/1996 | Batich et al. |
| 5,569,463 A | 10/1996 | Helmus et al. |
| 5,599,291 A | 2/1997 | Balbierz et al. |
| 5,599,298 A | 2/1997 | Sahatjian |
| 5,605,696 A | 2/1997 | Eury et al. |
| 5,607,417 A | 3/1997 | Batich et al. |
| 5,607,683 A | 3/1997 | Capelli |
| 5,611,354 A | 3/1997 | Alleyne |
| 5,616,119 A | 4/1997 | Davis |
| 5,616,608 A | 4/1997 | Kinsella et al. |
| 5,624,704 A | 4/1997 | Darouiche et al. |
| 5,628,780 A | 5/1997 | Helland et al. |
| 5,629,008 A | 5/1997 | Lee |
| 5,643,207 A | 7/1997 | Rise |
| 5,647,843 A | 7/1997 | Mesrobian et al. |
| 5,656,296 A | 8/1997 | Khan et al. |
| 5,676,972 A | 10/1997 | Galiatsatos et al. |
| 5,679,399 A | 10/1997 | Shlenker et al. |
| 5,693,034 A | 12/1997 | Buscemi et al. |
| 5,696,034 A | 12/1997 | Katayama et al. |
| 5,697,967 A | 12/1997 | Dinh et al. |
| 5,702,754 A | 12/1997 | Zhong |
| 5,707,366 A | 1/1998 | Solomon et al. |
| 5,716,406 A | 2/1998 | Farber |
| 5,741,331 A | 4/1998 | Pinchuk |
| 5,762,638 A | 6/1998 | Shikani et al. |
| 5,772,640 A | 6/1998 | Modak et al. |
| 5,788,687 A | 8/1998 | Batich et al. |
| 5,843,172 A | 12/1998 | Yan |
| 5,849,327 A | 12/1998 | Berliner et al. |
| 5,853,745 A | 12/1998 | Darouiche |
| 5,873,904 A | 2/1999 | Ragheb et al. |
| 5,877,224 A | 3/1999 | Brocchini et al. |
| 5,902,283 A | 5/1999 | Darouiche et al. |
| 5,908,413 A | 6/1999 | Lange et al. |
| 5,932,248 A | 8/1999 | Chen et al. |
| 5,945,115 A | 8/1999 | Dunn et al. |
| 5,985,307 A | 11/1999 | Hanson et al. |
| 5,989,463 A | 11/1999 | Tracy et al. |
| 6,001,386 A | 12/1999 | Ashton et al. |
| 6,013,853 A | 1/2000 | Athanasiou et al. |
| 6,039,967 A | 3/2000 | Ottoboni et al. |
| 6,060,534 A | 5/2000 | Ronan et al. |
| 6,083,208 A | 7/2000 | Modak et al. |
| 6,096,108 A | 8/2000 | Coulonvaux et al. |
| 6,106,505 A | 8/2000 | Modak et al. |
| 6,120,789 A | 9/2000 | Dunn |
| 6,143,314 A | 11/2000 | Chandrashekar et al. |
| 6,176,849 B1 | 1/2001 | Yang et al. |
| 6,179,817 B1 | 1/2001 | Zhong |
| 6,184,266 B1 | 2/2001 | Ronan et al. |
| 6,224,579 B1 | 5/2001 | Modak et al. |
| 6,248,129 B1 | 6/2001 | Froix |
| 6,258,121 B1 | 7/2001 | Yang et al. |
| 6,261,630 B1 | 7/2001 | Nazarova et al. |
| 6,262,115 B1 | 7/2001 | Guittard et al. |
| 6,270,053 B1 | 8/2001 | Eshel |
| 6,280,411 B1 | 8/2001 | Lennox |
| 6,299,597 B1 | 10/2001 | Buscemi et al. |
| 6,299,894 B1 | 10/2001 | Markkula et al. |
| 6,306,422 B1 | 10/2001 | Batich et al. |
| 6,316,018 B1 | 11/2001 | Ding et al. |
| 6,316,522 B1 | 11/2001 | Loomis et al. |
| 6,322,847 B1 | 11/2001 | Zhong et al. |
| 6,335,028 B1 | 1/2002 | Vogel et al. |
| 6,335,029 B1 | 1/2002 | Kamath et al. |
| 6,340,368 B1 | 1/2002 | Verbeck |
| 6,361,557 B1 | 3/2002 | Gittings et al. |
| 6,364,852 B1 | 4/2002 | Lee |
| 6,458,076 B1 * | 10/2002 | Pruitt .......................... 600/146 |
| 6,475,434 B1 | 11/2002 | Darouiche |
| 6,482,830 B1 | 11/2002 | Redkar et al. |
| 6,545,097 B2 | 4/2003 | Pinchuk et al. |
| 6,596,401 B1 | 7/2003 | Terry et al. |
| 6,638,917 B1 | 10/2003 | Li et al. |
| 6,641,831 B1 | 11/2003 | Schierholz |
| 6,693,089 B1 | 2/2004 | Li et al. |
| 6,706,024 B2 | 3/2004 | Modak et al. |
| 6,719,991 B2 | 4/2004 | Darouiche et al. |
| 6,746,481 B1 | 6/2004 | Larik et al. |
| 6,796,960 B2 | 9/2004 | Cioanta et al. |
| 6,887,270 B2 | 5/2005 | Miller et al. |
| 7,288,084 B2 * | 10/2007 | Li .............................. 604/890.1 |
| 2001/0007083 A1 | 7/2001 | Roorda |
| 2001/0007931 A1 | 7/2001 | Blatter |
| 2001/0010016 A1 | 7/2001 | Modak et al. |
| 2001/0029660 A1 | 10/2001 | Johnson |
| 2001/0041883 A1 | 11/2001 | Devonec |
| 2002/0031601 A1 | 3/2002 | Darouiche et al. |
| 2002/0045868 A1 | 4/2002 | Reever |
| 2002/0082679 A1 | 6/2002 | Sirhan et al. |
| 2002/0090388 A1 | 7/2002 | Humes et al. |
| 2002/0107330 A1 | 8/2002 | Pinchuk et al. |

(56) References Cited

U.S. PATENT DOCUMENTS

| | | |
|---|---|---|
| 2002/0165521 A1 | 11/2002 | Cioanta et al. |
| 2002/0188246 A1 | 12/2002 | Hayner et al. |
| 2003/0018306 A1 | 1/2003 | Bucay-Couto et al. |
| 2003/0024534 A1 | 2/2003 | Silvestri et al. |
| 2003/0040754 A1 | 2/2003 | Mitchell et al. |
| 2003/0060877 A1 | 3/2003 | Falotico et al. |
| 2003/0078242 A1 | 4/2003 | Raad et al. |
| 2003/0153983 A1* | 8/2003 | Miller et al. ............... 623/23.7 |
| 2003/0199993 A1 | 10/2003 | Gellman et al. |
| 2003/0203991 A1 | 10/2003 | Schottman et al. |
| 2003/0224033 A1 | 12/2003 | Li et al. |
| 2004/0022824 A1 | 2/2004 | Li et al. |
| 2004/0166094 A1 | 8/2004 | Darouiche et al. |
| 2004/0166102 A1 | 8/2004 | Darouiche et al. |
| 2004/0186377 A1* | 9/2004 | Zhong et al. ............... 600/431 |
| 2004/0208908 A1 | 10/2004 | Modak et al. |
| 2004/0215169 A1* | 10/2004 | Li ............................... 604/537 |
| 2004/0230156 A1 | 11/2004 | Schreck et al. |
| 2004/0249441 A1 | 12/2004 | Miller et al. |
| 2005/0063907 A1* | 3/2005 | Brandon et al. ............ 424/9.4 |
| 2005/0064008 A1 | 3/2005 | Bucay-Couto et al. |
| 2005/0064045 A1 | 3/2005 | Zhong et al. |
| 2007/0038292 A1* | 2/2007 | Danielpour ................. 623/1.42 |

FOREIGN PATENT DOCUMENTS

| | | |
|---|---|---|
| EP | 0 328 421 A2 | 8/1989 |
| EP | 0 379 271 A2 | 7/1990 |
| EP | 0 734 721 A | 10/1996 |
| EP | 0 734 721 A2 | 10/1996 |
| EP | 0818207 A2 | 1/1998 |
| EP | 0 970 711 A2 | 1/2000 |
| EP | 1 247 537 A1 | 10/2002 |
| GB | 2152382 A | 8/1985 |
| GB | 2319507 A | 5/1998 |
| WO | WO 8601813 A1 | 3/1986 |
| WO | WO 93/05730 | 4/1993 |
| WO | WO 93/10847 | 6/1993 |
| WO | WO 95/06487 A2 | 3/1995 |
| WO | WO 95/08305 A1 | 3/1995 |
| WO | WO 97/14447 A1 | 4/1997 |
| WO | WO 98/34669 | 8/1998 |
| WO | WO 98/36784 | 8/1998 |
| WO | WO 99/24391 | 5/1999 |
| WO | WO 99/47595 A1 | 9/1999 |
| WO | WO 00/62830 A2 | 10/2000 |
| WO | WO 01/03607 A2 | 1/2001 |
| WO | WO 01/21229 A1 | 3/2001 |
| WO | WO 02/21913 A2 | 3/2002 |
| WO | WO 02/43788 | 6/2002 |
| WO | WO 02/078778 A1 | 10/2002 |
| WO | WO 03/066119 A1 | 8/2003 |

OTHER PUBLICATIONS

Wu, Benjamin M. et al., "Solid free-form fabrication of drug delivery devices" Journal of Controlled Release, 1996, 77-87, 40, Elsevier Science B.V.

Bridge, R., "Poly Extrusion" Honors Project for Chemical Engineering at University of Connecticut (online), May 1997 (retrieved on Feb. 11, 2002). Retrieved from the Internet: http://www.engr.uconn.edu/cheg/cheg_c256hnp.htm.

Harris, L., "Injection Molding" Honors Project for Chemical Engineering at University of Connecticut (online), May 1997 (retrieved on Feb. 11, 2002). Retrieved from the Internet: http://www.engr.uconn.edu/cheg/cheg_injmold.htm#Equipment.

Langer, R., "Drug Delivery Targeting" Nature, 1998, 5-9, 392.

The Merck Index: An Encyclopedia of Chemicals, Drugs, and Biologicals, Merck Research Laboratories, 1996, 932, 12$^{th}$ Edition.

Notification of Transmittal of the International Search Report and the Written Opinion of the International Searching Authority, or the Declaration dated Oct. 4, 2007 for International Application No. PCT/US2007/000022, filed Jan. 2, 2007 (14 pages including cover page).

Notification Concerning Transmittal of International Preliminary Report on Patentability (Chapter 1 of the Patent Cooperation Treaty) mailed Jul. 17, 2008 issued in corresponding international application No. PCT/US2007/000022.

Donald P. Griffith et al., "Urease: The Primary Cause of Infection-Induced Kidney Stones," Investigative Urology, vol. 13(5), Mar. 1976, pp. 346-350.

J. Regos et al., "Antimicrobial Spectrum of Triclosan, a Broad-Spectrum Antimicrobial Agent for Topical Application II. Comparision with Some Other Antimicrobial Agents", Dermatologica, vol. 158, 1979, pp. 72-79.

Edward S. Wong et al., Guideline for Prevention of Catheter-associated Urinary Tract Infections http://www.cdc.gov, Feb. 1981.

Gristina et al., "Bacterial Adherence and the Glycocalyx and Their Role in Musculoskeletal Infection," Orthopedic Clinics of North America, vol. 15, No. 3, Jul. 1984, pp. 517-535.

Parsons, C. Lowell et al., "Inhibition of Sodium Urate Crystal Adherence to Bladder Surface by Polysaccharide," Journal of Urology, vol. 134, No. 3, Sep. 1985, pp. 614-616.

Kingston, D. et al., "Self-disinfecting Plastics for Intravenous Catheters and Prosthetic Inserts," Journal of Hygiene, Cambridge, vol. 96, 1986, pp. 185-198.

Speer, a.G. et al., "The Role of Bacterial Biofilm in Clogging of Bilary Stents," Dept. Gastroenterology, Middesex Hospital, London UK, Dept. Biology, University of Calgary Alberta, Canada, Gastrointest Endosc. 1986, 32:156.

Costerton, J. William et al., " Bacterial Biofilms in Nature and Disease," Annual Review of Microbiology, vol. 41, 1987, pp. 435-464.

Farber, B.F. et al., "Unique Properties of *S. epidermidis* Extractable Polysaccharide Slime (SEEP)," Clinical Research, vol. 36, No. 3, 1988, p. 455A.

Doughterty, Steven H. et al., "Endogenous Factors Contributing to Prosthetic Device Infections," Infectious Disease Clinics of North America, vol. 3, No. 2, Jun. 1989, pp. 199-209.

Liedberg H. et al., "Silver Coating of Urinary Catheters Prevents Adherence and Growth of *Pseudomonas Aeruginosa*," Urological Research, vol. 17, No. 6, 1989, pp. 357-358.

Ramsay, J.W.A. et al., "Biofilms Bacteria and Bladder Catheters: A Clinical Study," British Journal of Urology, vol. 64, No. 4, Oct. 1989, pp. 395-398.

Farber, Bruce et al., "*Staphylococcus epidermidis* Extracted Slime Inhibits the Antimicrobial Action of Glycpeptide Antibiotics," Journal of Infectious Diseases, vol. 161, No. 1, Jan. 1990, pp. 37-40.

Dunne, W. Michael Jr., "Effects of Subinhibilory Concentrations of Vancomycin or Cefamandole on Biofilm Production by Coagulase-Negative *Staphylococci*," Antimicrobial Agents and Chemotherapy, vol. 34, No. 3, Mar. 1990, pp. 390-393.

Anwar, Hosmin et al., "Testing the Susceptibility of Bacteria in Biofilms to Antibacterial Agents," Antimicrobial Agents and Chemotherapy, vol. 34, No. 34, 1990, pp. 2043-2046.

Liedberg, H. et al., "*Pseudomonas aeruginosa*: Adherence to and Growth on Different Urinary Catheter Coatings," International Urology and Nephrology, vol. 22, No. 5, 1990, pp. 487-492.

Farber, B.F. et al., "Extracted *S. epidermidis* Slime Interferes with Antimicrobial Action of Glycopeptide Antibiotics," Clinical Research, vol. 37, No. 2, 1990, p. 428A.

Farber, B.F. et al,, "*Staphylococcus aureas* Extracted Polysaccharide Interferes with Antimicrobial Action of Glycopeptide Antibiotics," Clinical Research, vol. 38, No. 2, 1990, p. 428A.

Stamm, Walter E., "Catheter-Associated Urinary Tract Infections :Epidemiology, Pathogenesis and Prevention," American Journal of Medicine, vol. 91, No. 3B, Sep. 1991, pp. 65S-71S.

Golomb, Gershon et al., "Prevention of Bacterial Colonization on Polyurethane in vitro by Incorporated Antibacterial Agent," Journal of Biomedical Materials Research, vol. 25, No. 8, Aug. 1991, pp. 937952.

Mulhall, Anne, "Biofilms and Urethral Catheter Infections," Nursing Standard, vol. 5, No. 18, Jan. 23-29, 1991, pp. 26-28.

Chang, Chung Che et al., "Effect of *Staphylococcus epidermidis* on Adherence of *Pseudomonas aeruginosa* and *Proteus mirabilis* to Polymethyl Methacrylate (PMMA) and Gentamicin-Containing PMMA," Journal of Orthopedic Research, vol. 9, No. 2, Mar. 1991, pp. 284-288.

(56) References Cited

OTHER PUBLICATIONS

Swartz, R. et al., "Biofilm Formation on Peritoneal Catheters Does Not Require the Presence of Infection," ASAIO Trans., vol. 37, No. 4, Oct.-Dec. 1991, pp. 626-634.

Richards, G.K. et al., "Comparative Rates of Antibiotic Action Against *Staphylococcus epidermidis* Biofilms," ASAIO Trans., vol. 37, No. 3, Jun.-Sep. 1991, pp. M160-162.

Ikeda, F. et al., "Formation of Biofilm by Slime Producing *Staphylococcus epidermis* and bacterial Activity of Cefazolin," Kasenshogaku Zasshi. Journal of the Japanese Association for Infectious Diseases, vol. 65, No. 7, Jul. 1991, pp. 875-882,.

Farber, Bruce F. et al., "The Use of Nonsteroidal Antiinflammatory Drugs to Prevent Adherence of *Staphylococcus epidermidis* to Medical Polymers," Journal of Infectious Diseases, vol. 166, No. 4, Oct. 1992, pp. 861-865.

Donnenfeld, E.D. et al., "Biofilm and Bacterial Adherence Inhibition with Sodium Salicylate," Investigative Ophthalmology & Visual Science, vol. 35, No. 4, 1994, p. 2164.

Teichberg, Saul et al., "Salicylic Acid Decreases Extracellular Biofilm Production by *Staphylococcus epidermidis*: Electron Microscope Analysis," Journal of Infectious Diseases, vol. 167, No. 6, 1994, pp. 1501-1503.

Roberts, E.L. et al., "The Role of Sodium Salicylate in the Prevention of Adherence of Acanthamoeba Castellanii to Unworn Contact Lenses," Investigative Ophthalmology & Visual Science, vol. 35, No. 4, 1994, p. 2150.

Farber, Bruce F. et al., "A Novel Antibiofilm Technology for Contact Lens Solutions," Ophthalmology, vol. 102, No. 5, May 1995, pp. 831-836.

Donnefeld, Eric D. et al., "Controlled Evaluation of a Bandage Contact lens and a Topical Nonsteroial Antiinflammatory Drug in Treating Traumatic Corneal Abrasions," Ophthalmology, vol. 102, No. 6, Jun. 1995, pp. 979-984.

Sherman, Stuart et al., "Stent-induced Pancreatic Ductal and Parenchymal Changes: Correction of Endoscopic Ultrasound with ERCP," Gastrointestinal Endoscopy, vol. 44, No. 3, 1996, pp. 276-282.

Taniguchi, Takumi et al., Lidocaine attenuates the hypotensive and inflammatory responses to endotoxemia in rabbits, Critical Care Medicine, vol. 24(4), Apr. 1996, pp. 642-646.

H.N. Bhargava et al., "Triclosan: Applications and Safety," American Journal of Infection Control, vol. 24(3), Jun. 1996, pp. 209-218.

Theodorou C. et al., "Incontinence after surgery for benign prostatic hypertrophy: The case for complex approach and treatment," (abstract), 1998.

Speer, Anthony G. et al., "Biliary Stent Blockage with Bacterial Biofilm," Annals of Internal Medicine, vol. 108, No. 108, No. 4, Apr. 1998, pp. 546-553.

Alain Meyrier, Urinary Tract Infections, vol. II, Chapter 7 of The Schrier Atlas of Diseases of the Kidney, ed. Robert W. Schrier, 1999.

Ciba Specialty Chemicals Chiba® IRGASAN® DP 300, Chiba® IRGACARE® MP. Antimicrobial active ingredient for personal care products, 2001, 16 pages.

Vasudev, Sindhu C. et al., Development of chitosan/polyethylene vinyl acetate co-matrix: controlled release of aspirin-heparin for preventing cardiovascular thrombosis, Biomaterials, 1997, vol. 18, No. 5, pp. 375381.

Gonzalez, Alex et al., Minimizing Hospital Length of Stay in Children Undergoing Ureteroneocystostomy, Urology 52(3) 1998, pp. 501-504.

Liu, JS, Hrebinko, RL., J Urol., Jan. 1998 159(1), abstract, 1 page.

Fowler, Clare J., Urology 55 (Suppl 5A), 2000, pp. 60-64.

Konety, Badrinath et al., Urolume Stent Placement for the treatment of postbrachytherapy bladder outlet obstruction, Urology 55, 2000, pp. 721-724.

Olweny, Ephrem O. et al., Evaluation of a chronic indwelling protype mesh ureteral stent in a porcine model, Urology 56(5), 2000, pp. 857-862.

Rhonda D. Jones et al., "Triclosan: A Review of Effectiveness and Safety in Health Care Settings," American Journal of Infection Control, vol. 28(2), Apr. 2000, pp. 184-196.

Arda, Serdar et al., Journal of Pediatric Surgery, vol. 36, No. 12, Dec. 2001, pp. 1829-1831.

Young-Gi et al., Radiology, Apr. 2002, 223, pp. 83-90.

Stephen Rothenburger et al., "In Vitro Antimicrobial Evaluation of Coated VICRYL Plus Antibacterial Suture (Coated Polyglactin 910 with Triclosan) Using Zone of Inhibition Assays," Surgical Infections, vol. 3, Supplement, 2002, pp. S79-S87.

Medscape, Products and Devices in the Management of Urinary Incontinence: Indwelling Urinary Catheters and External Catheters, Society of Urological Nurses and Associates, 2003, pp. 1-3.

Allan Ronald, "The Etiology of Urinary Tract Infection: traditional and Emerging Pathogens," Dis. Mon, vol. 49, 2003, pp. 71-82.

D.J. Stickler et al., "Control of Encrustation and Blockage of Foley Catheters," The Lancet, vol. 361, Apr. 2003, pp. 1435-1437.

Ciba Specialty Chemicals Chiba® IRGASAN® DP 300, Chiba® IRGACARE® MP Antimicrobials Toxicological and ecological data; Official registrations, Jan. 2003, 16 pages.

Percuflex® Tail Plus ™ Tapered Ureteral Stent. Boston Scientific. Urology. http://www.bostonscientific.com/med_specialty/deviceDetail.jhtml?task=tskBasicDevice.ihtml&s Feb. 24, 2004 download.

Ketorolac. The Merck Index. 14$^{th}$ Ed. Accessed online Nov. 3, 2008 at http://themerckindex.cambridgesoft.com/TheMerckIndex/index/asp.

Oxybutynin. The Merck Index. 14$^{th}$ Ed. Accessed online on Nov. 3, 2008 at http://the MerckIndex.cambridgesoft.com/TheMerckIndex/index.asp.

Instill, Merriam-Webster, Apr. 13, 2011, pp. 1 and 2.

\* cited by examiner

MEDICAL IMAGING REFERENCE DEVICES

CROSS-REFERENCE TO RELATED CASES

This application is a continuation-in-part of U.S. patent application Ser. No. 10/209,476 (which was published as US 2004-0022824 A1 on Feb. 5, 2004), the entirety of which is incorporated herein by reference. U.S. patent application Ser. No. 10/424,621 (which was published as US 2004-0215169 A1 on Oct. 28, 2004) also is incorporated in its entirety herein by reference.

TECHNICAL FIELD

The present invention generally relates to medical devices, and in particular, medical devices that can be used to determine the location of points of interest within the body of a human or other mammal.

BACKGROUND INFORMATION

Magnetic Resonance Imaging (MRI) and ultrasound are the two most widely used real-time in vivo imaging systems/techniques for guiding a biopsy device to a location within the body of a patient. Other techniques include fluoroscopy, radiography, computed axial tomography (CAT or CT), and positron emission tomography (PET). Once the device reaches the location of interest, within the body, a tissue sample is obtained with the device. The device with the sample is then removed from the body.

The state of the tissue sample (e.g., cancerous or normal) is then determined by histology. If the sample is abnormal (e.g., cancerous), it is then necessary to return to the site from which the sample was taken to treat the site. It is difficult however to reposition properly the patient and to return to the same location to allow treatment at the exact location of the abnormal biopsy.

SUMMARY OF THE INVENTION

The invention generally relates to determining accurately the location at which a biopsy has been taken, to allow treatment to be administered to that precise location where the biopsy (post-extraction examination of which has revealed the presence of cancerous or otherwise abnormal tissue) was taken.

In one aspect, the invention is directed to an imaging reference device that includes an elongated body member and an enclosed internal space defined in the elongated body member. An imaging agent is disposed within the space, and the agent can be visualized from outside of a body of a patient by use of an imaging system while the device is within the body of the patient.

In one embodiment according to this aspect of the invention, the imaging reference device comprises a lumen disposed longitudinally through the elongated body member for allowing bodily fluids to pass therethrough. The lumen may be eccentric with respect to the elongated body member and/or substantially parallel to the enclosed internal space.

In other embodiments, the enclosed internal space extends along substantially the entire length of the elongated member. The enclosed internal space may be in an eccentric relationship with respect to the elongated member. Alternatively, the enclosed internal space can be disposed perpendicularly with respect to the elongated member.

There may be more than one enclosed internal space defined in the elongated body member, and one or more imaging agents disposed in the enclosed internal spaces. The enclosed internal spaces may be substantially parallel to each other or the enclosed internal spaces may be arranged in such a manner as to form a cross-hairs or a grid-like cross sectional profile. The elongated member and enclosed internal spaces may have variously shaped cross sectional profiles. In some embodiments, the cross sectional profile of the elongated body member is substantially circular or substantially elliptical. In some embodiments, the cross sectional profile of the enclosed internal space is substantially circular or substantially elliptical.

The imaging agent can be, or can include, a radio opaque material, a contrast agent (including a negative or a positive contrast agent), a gadolinium containing contrast agent, a contrast agent including one or more complexes of gadolinium, iron oxide, an iron containing contrast agent, a contrast agent including one or more substances having magnetic resonance, a dye, or any other substance that can be visualized externally (that is, external to the body of the patient) by an imaging system including, but not limited to, an MRI system, an ultrasound system, a PET system, a CT scan system, or an infrared (IR) system.

The imaging agent can be in the form of a powder, particulates, a liquid, a solid, a gel, macro bubbles, micro bubbles, a rod, or combinations thereof.

In another aspect, the invention relates to an imaging reference device that includes a polymeric matrix forming the device and an imaging agent contained within at least some of the spaces of the matrix. The imaging agent can be visualized from outside a body of a patient by use of an imaging system when the device is within the body of the patient. The matrix comprises polymer macromolecules and has the spaces between the macromolecules.

The matrix can be biocompatible, and it may be biodegradable or bioerodable within the body of the patient.

The device can be compressible and/or expandable. It can be configured to expand upon hydration. The medical device also can be configured to have hydrophobic or hydrophilic properties, and it can be formulated in a polymeric skeletal structure.

The polymeric matrix can be configured to include protuberances for holding the imaging reference device in place within the body of the patient. The device can take the form of one or more pellets, tissue clips, sutures, or rings, for example. A biodegradable or otherwise erodable polymeric matrix can be made of poly(lactide) co-glycolide and other polyesters, poly (ortho esters), polyanhydrides, polydioxanones, polyphosphazenes, polyhydroxybutyrate (PHB) and copolymers, polyhydroxyvalerate (PHV) and copolymers, acrylic polymers, polyamino acids, polyethylene glycol (PEG), polyethylene oxide (PEO), polylactic-glycolic acid and polyethylene glycol (PLGA-PEG) and other block or multiblock copolymers, polyvinyl acetate (PVA), and natural polymers like chitosan, alginate, dextran and other starch materials, and celluloses, for example. A non-degradable polymeric matrix can be made of ethylene vinyl acetate (EVA), for example.

The imaging agent can be or include a radio opaque material, a contrast agent (including a negative or a positive contrast agent), a gadolinium containing contrast agent, a contrast agent including one or more complexes of gadolinium, iron oxide, a iron containing contrast agent, a contrast agent including one or more substances having magnetic resonance, a dye, or any other substance that can be visualized externally by an imaging system including, but not limited to, an MRI system, an ultrasound system, a PET system, a CT scan system, or an IR system.

The imaging agent can be in the form of a powder, pellets, particulates, a liquid, a solid, a gel, macro bubbles, micro bubbles, a rod, or combinations thereof.

In yet another aspect, the invention involves a medical device for placement in a body of a patient wherein the device includes a body member formed of a biocompatible polymer and an imaging agent incorporated therein. The imaging agent is capable of being visualized from the outside of the body of the patient by use of an imaging system to locate the device when the device is disposed within the body of the patient.

The imaging agent can be contained in a chamber defined in the body member of the aforementioned medical device, or integrated in the biocompatible polymer, or both, among other things. Preferably, the imaging agent is of the type that can be visualized by an imaging system (using, for example, MRI, CT, PET, or ultrasound technology) when the device is disposed within the body of the patient.

In another embodiment of the aforementioned medical device, the device can also include a substance disposed with the imaging agent in the body member or chamber. Alternatively, the additional substance can be contained in a separate chamber without the imaging agent within the body member or separately integrated without the imaging agent in the biocompatible polymer. The additional substance can be selected to provide a therapeutic benefit to the patient or affect the properties of the biocompatible polymer, among other things.

In still another aspect, the invention is directed to an imaging guide device or marker that can be placed on or adhered to the surface of the skin of a patient. The device or marker can be made of, contain, or house an imaging agent that can be visualized by using an imaging system external to the patient's body. The device or marker can house, contain, or be made of more than one imaging agent which allows the device or marker to be visualized with any one of a plurality of different imaging systems. Such a surface device or marker can be non-degradable and can be made from ethylene vinyl acetate (EVA), silicon, polycarbonates, or some other biocompatible material. The device or marker can be made to adhere to the skin surface of a patient by, for example, the use of a biocompatible adhesive disposed on one side of the device or marker. Such a surface device or marker can be made in any of a variety of shapes including, for example, a triangle, a square, a diamond, a circle, etc., and it can be flat and thin enough so that it does not protrude too much or much at all from the surface of the skin to which it is adhered.

These and other aspects, features, and advantages of the invention will become more readily apparent from the following drawings and detailed description.

BRIEF DESCRIPTION OF THE DRAWINGS

To allow the invention and various disclosed embodiments in accordance with the invention to be more readily understood, including how to make and use devices, methods, and systems of the invention, the following detailed description refers to the following drawings, wherein.

DESCRIPTION

The following detailed description is provided to illustrate various embodiments of the invention, but the detailed description is not intended to limit the scope of the invention.

In accordance with the present invention, a medical device configured for placement in or on the body of a patient (typically a human or other mammal) includes one or more imaging agents that assist in locating a point of interest within the patient. Medical devices of the present invention, such as, for example, a stent, catheter, dialysis tube, cannula, suture, clip, access sheath, balloon, or other device suitable for placement in or on a patient, can be constructed, modified, or retrofitted to include one or more imaging agents in accordance with the present invention. The imaging agent(s) may also be loaded or replaced in a medical device in accordance with the present invention.

In one aspect of the invention, an imaging guide device or marker can be configured to be placed on or adhered to the surface of the skin of a patient. Such a device or marker can be made of, contain, or house an imaging agent that can be visualized by using an imaging system external to the patient's body. The device or marker can house, contain, or be made of more than one imaging agent which allows the device or marker to be visualized with any one of a plurality of different imaging systems. Such a surface device or marker can be non-degradable and can be made from ethylene vinyl acetate (EVA), silicon, polycarbonates, or some other biocompatible material. The device or marker can be made to adhere to the skin surface of a patient by, for example, the use of a biocompatible adhesive disposed on one side of the device or marker. Such a surface device or marker can be made to have any of a variety of shapes including, for example, a triangle, a square, a diamond, a circle, etc., and it can be flat and thin enough so that it does not protrude too much or much at all from the surface of the skin to which it is adhered.

The imaging agent itself, or by the addition to it of at least one substance, can be visualized externally while the device is within the body of a patient. A plurality of such imaging agents can be mixed together and then disposed together in the device, or each such agent can be disposed in a separate location in the device. The visualization can be achieved with the use of one or more imaging systems. Each of the imaging agents may come in various forms, such as a liquid, gel, solid, powder, particulate, macro or micro bubbles, or rod formulation, or the like, and it can be biodegradable. Suitable imaging agents may include one or more substances such as gadolinium containing contrast agents, contrast agents including one or more complexes of gadolinium, iron oxide, iron containing contrast agents, contrast agents including one or more substances having magnetic resonance, radio opaque materials, dyes, or any other imaging substances or contrast agents (including negative or positive contrast agents), that can be visualized by imaging systems such as an MRI system, an ultrasound system, a PET system, a CT scan system, or an IR system.

By using devices constructed according to the present invention, doctors or other medical professionals/practitioners can remove a small sampling of tissue from a patient (i.e., a biopsy), bring the tissue or have it brought to another location (that differs from the location in which the procedure was conducted) to be tested, get the results from the testing, and then locate precisely the spot at which the tissue was removed from the patient's body. Assuming the tissue was tested and found to be abnormal, the present invention significantly eases the procedure involved with treating the remaining abnormal tissue in the body by providing a visual aid to use as a reference point as to where treatment should occur within the patient's body.

For example, the medical device with the imaging agent(s) can be placed in the patient to mark the location within the patient's body where tissue is removed at the time of removal. The imaging agent(s) within the medical device can then be viewed by the physician on an external video screen, computer monitor, or the like, while the physician manipulates surgical implements in the patient's body. Thus, a medical device of the present invention can be used during surgical procedures to provide real-time assistance in determining the location at which further tissue removal is necessary.

Additionally, one or more medical devices with one or more imaging agents incorporated therein in accordance with the present invention can be positioned in a patient at the location in the body where one or more tissue samples are taken, and used thereafter in conjunction with visualization devices as points of reference to determine the location or area in which the samples where taken, for real-time distance and angle measurements via anterior and/or cross sectional views.

Figure 1A:
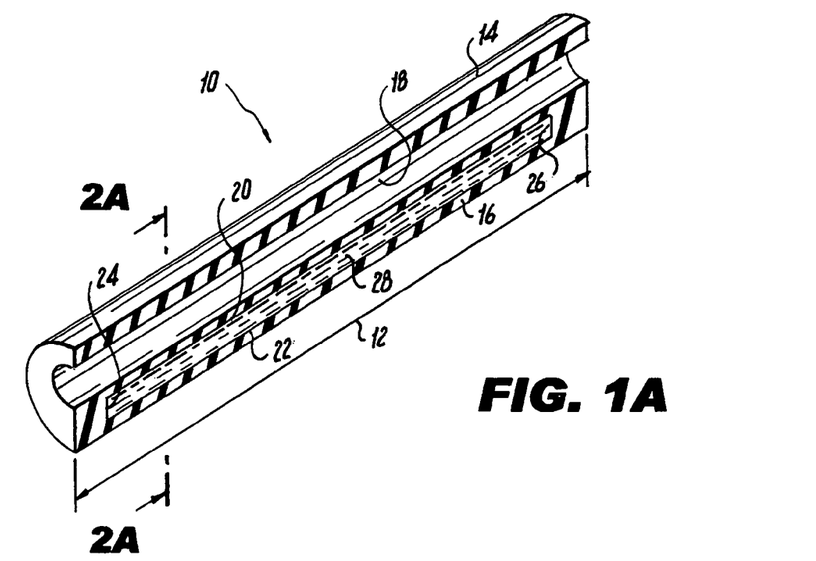
FIG. 1A is a schematic longitudinal cross-section of an exemplary medical device, in particular a stent that includes an imaging agent and that is constructed in accordance with an embodiment of the present invention.

Illustrative examples of medical devices constructed in accordance with the present invention are discussed herein below. FIG. 1A shows a longitudinal cross-section of a stent 10 constructed in accordance with the present invention that can be placed in the urinary system of a patient. Stent 10 includes an elongated member 12 including opposing outer wall portions 14 and 16. An inner passage 18 defined by the inner surface of outer wall portion 14 and an inner wall portion 20 extends longitudinally through elongated member 12. Stent 10 also includes an enclosed internal space 22 defining a volume adjacent to passage 18 within elongated member 12. In this embodiment, enclosed internal space 22 is defined between inner wall portion 20 and the inner surface of outer wall portion 16, and by ends 24 and 26, respectively. An imaging agent 28 can be disposed within at least a portion of enclosed internal space 22. In operation, stent 10 maintains a flow of bodily fluids through passage 18 when the stent 10 is placed within a patient's body such as within the patient's prostatic urethra.

The present invention can also provide a vehicle to deliver one or more substances that provide a therapeutic benefit to the body of a patient. In general, a therapeutic substance for use in connection with the present invention can be any pharmaceutically acceptable therapeutic agent. The agent is pharmaceutically acceptable in that it is approved, or is capable of being approved, by the United States Food and Drug Administration or Department of Agriculture for use in humans or animals when incorporated in or on an implantable or insertable medical device. The therapeutic agent can be one or more anti-inflammatory compounds, analgesic compounds, local anesthetic compounds, antispasmodic compounds, antineoplastics, antimicrobials, antibiotics, pharmaceutical drugs, or some combination thereof.

Figure 1B:
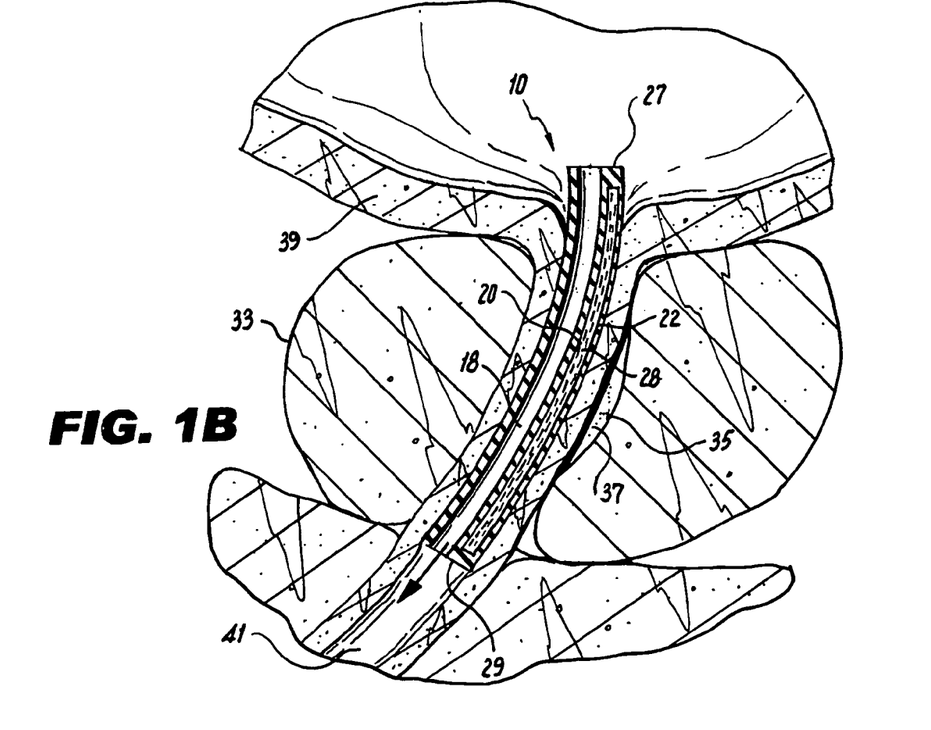
FIG. 1B illustrates the stent of FIG. 1A placed in the prostatic urethra of a patient's body.

Stent 10 can be configured to release imaging agent 28, along with any other additional substances in enclosed internal space 22, such as drugs that provide a therapeutic benefit, into the patient's body. This may be accomplished by various mechanisms, such as, for example, by configuring stent 10 to allow imaging agent 28 and/or substances to diffuse through walls 16 and 20, or both of stent 10. Stent 10 may also be configured to withhold release of imaging agent 28, or withhold release of imaging agent 28 while allowing the release of other substances included with imaging agent 28 in enclosed internal space 22. The methods for inserting a medical device such as stent 10 or other embodiments of the invention discussed herein may vary according to the particular application for which the device is intended. For example, if a tissue sample was taken from the prostate 33 of a patient at biopsy location 35, stent 10 can be placed in the prostatic urethra 37 of the patient adjacent biopsy location 35, as shown in FIG. 1B. Stent 10 maintains an open passageway therethrough and imaging agent 28 in enclosed space 22 facilitates finding biopsy location 35 again, if necessary, after the tissue sample is tested. While the sample is being tested, passage 18 in stent 10 allows urine to pass from the bladder 39 into the urethra 41, as shown by the arrow in FIG. 1B.

Insertion of stent 10 in prostatic urethra 37 may be accomplished according to the basic steps described herein below. A medical professional or physician inserts a first end 27 of stent 10 into the patient's meatus. To advance stent 10 into urethra 41, the physician will typically use a pusher or stylet (both not shown) that includes a shoulder portion (not shown) for abutting the other or second end 29 of stent 10. The shoulder portion provides leverage and support for advancing stent 10 through the patient's urinary tract. To couple the stylet to stent 10, the physician inserts the pusher into at least a portion of passage 18 via the opening adjacent second end 29 of stent 10. Accordingly, the other diameter of the stylet must be smaller than the diameter of passage 18.

Next, the physician advances the stylet through passage 18 until the stylet's shoulder portion abuts second end 29 of stent 10. The stylet should be long enough such that a portion thereof remains outside the patient's body when stent 10 is properly positioned within the urinary system of the patient. By applying force to the stylet, the physician advances both the stylet and stent 10 through the urethra until first end 27 of stent 10 is located substantially within the bladder and second end 29 is proximal to the external sphincter, as shown in FIG. 1B.

To protect the patient's urethra from irritation, the medical professional may insert stent 10 into a sheath (not shown) prior to inserting stent 10 into the patient's body. The sheath is a smooth tubular member sized to receive stent 10. The leading portion of the sheath can include a tapered tip, which facilitates passage through a bodily lumen. A retraction device can be coupled to the sheath for removing the sheath from the patient after stent 10 is inserted into the patient. The retraction device can be a thread-like structure that is disposed in the urethra and extends outside of the patient while a medical professional inserts stent 10 into the patient's body.

Once stent 10 is properly positioned in the patient's body at, for example, the location at which a portion of tissue is removed, the physician removes the sheath by drawing the retraction device out of the body. The drawing action causes stent 10 to pass through an opening in the tip of the sheath and remain positioned in the desired location. When drawing the sheath retraction structure out of the body, a sufficient amount of counterforce should be applied to the stylet to maintain the proper position of stent 10. After the sheath is removed from the patient, the stylet may be retrieved from the patient's body. The stent 10 can be inserted into the body by other known methods.

Imaging agent 28 disposed in internal space 22 allows the physician to monitor the location of stent 10 within the patient's body, as shown in FIG. 1B. In this example, imaging agent 28 is a substance that can be visualized on a conventional MRI system, such as MRI system 80 shown in FIG. 1C. In other embodiments, the location of the stent 10 can be determined by visualizing the imaging agent 28 incorporated therein by using another imaging system such as an ultrasound system, a PET system, a CT scan system, or an IR system, for example. The MRI system 80 can be an open system or a closed system, and it can be used with a transrectal probe for better resolution.

Figure 1C:
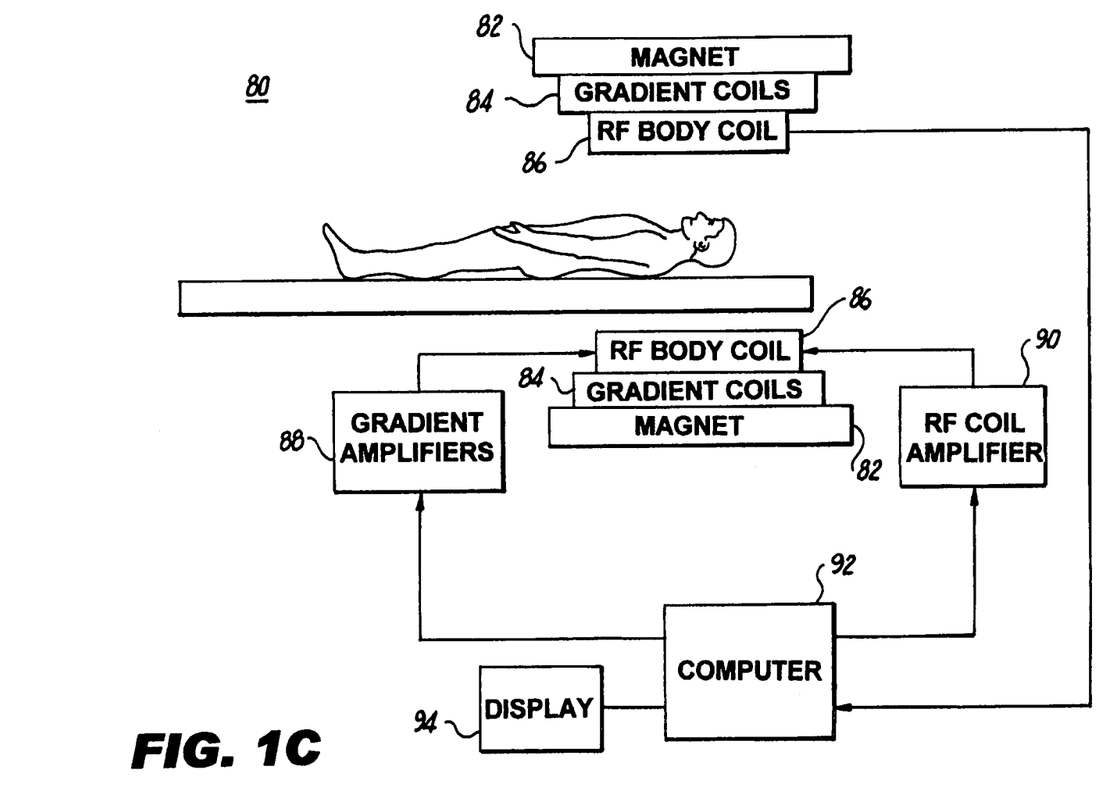
FIG. 1C is an illustration of a Magnetic Resonance Imaging (MRI) system that can be used to visualize the imaging agent disposed in a medical device placed in a body of a patient.

MRI system 80 includes a magnet 82, gradient coils 84, and a Radio Frequency (RF) body coil 86. The magnet 82 typically is made of a super-conducting material having a magnetic field strength of about 1.5 Tesla or higher. MRI system 80 further comprises gradient amplifiers 88, an RF coil amplifier 90, a computer 92 for controlling MRI system 80, and a display 94 for displaying MRI images.

Gradient amplifiers 88 are coupled between computer 92 and gradient coils 84, and are used to amplify control signals from computer 92 to gradient coils 84. RF coil amplifiers 90 are coupled between computer 92 and RF body coil 86, and are used to amplify signals from computer 92 to RF body coil 86.

To image inside a human body using MRI system 80, the patient is placed on a table 96, which can slide to a position within magnet 82 and RF body coil 86. MRI system 80 is capable of imaging a volume of the patient's body located within magnet 82 and the RF body coil 86. Gradient coils 84 apply a linear magnetic field gradient to the magnetic field of magnet 82. Computer 92 controls the slope and/or direction of the magnetic field gradient applied by gradient coils 84. The magnetic field gradient causes hydrogen atoms at different positions inside the human body to exhibit slightly different resonance frequencies. Computer 92 then transmits a pulse signal to RF body coil 86 via RF coil amplifiers 90. The pulse signal causes RF body coil 86 to transmit a magnetic pulse through the body in a direction that rotates the magnetic moment vectors of the hydrogen atoms away from the magnetic field of the magnet 82, thereby exciting the hydrogen atoms to a higher energy state.

When the magnetic pulse ceases, the hydrogen atoms relax back to a lower energy state in a process called Free Induction Decay (FID). During FID, the hydrogen atoms emit RF signals at their resonance frequencies. Due to the applied magnetic field gradient of the gradient coils 84, the hydrogen atoms at different positions inside the body emit RF signals at slightly different resonance frequencies. Similarly, imaging agent 28 disposed in stent 10 emits an RF signal at a differing resonance frequency that allows it to standout against the RF signals generated by the body. RF body coil 86 detects the emitted RF signals from the body and imaging agent 28, and outputs the detected RF signals to the computer 92. Computer 92 processes the detected RF signals to generate an image of the interior of the body, along with the location of imaging agent 28, which is displayed on the display 94. Computer 92 is able to determine at which position each detected RF signal was emitted by correlating the resonance frequency of the RF signal with information about the applied magnetic field gradient. MRI system 80 typically takes several measurements at different magnetic field gradients to generate an MRI image.

To better image a localized region of a human body, a small surface RF coil (not shown) may be used in conjunction with the MRI system 80 in FIG. 1C. In this arrangement, the small surface RF coil is positioned near a localized region of the human body. RF body coil 86 then transmits a magnetic pulse through the localized region of the body to cause the localized region to emit RF signals. RF body coil 86 may also have the ability to receive RF signals. The small surface RF coil detects the emitted RF signals within the localized region. An advantage of using a small surface RF coil to detect the emitted RF signals is that it typically has a better Signal-to-Noise Ratio (SNR) than the RF body coil 86.

Figure 2A:
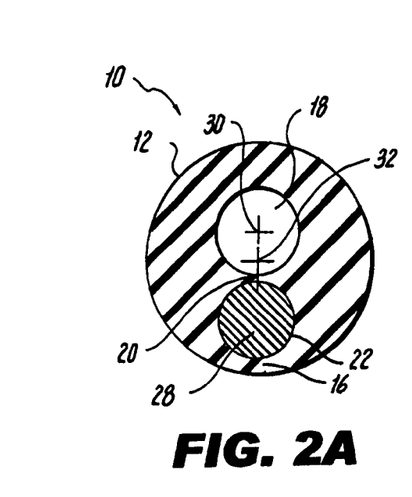
FIG. 2A is a schematic transverse cross-sectional view of the stent of FIG. 1A taken at line 2A-2A.

FIG. 2A is a cross-section of stent 10 of FIG. 1A taken at line 2A-2A. To maximize the volume of enclosed internal space 22, among other things, center axis 30 of the passage 106 is positioned off-center or eccentric relative to center axis 32 of elongated member 12. In this embodiment, enclosed internal space 22 is disposed adjacent to the passage 18 and is also positioned off-center relative to center axis 30 of elongated member 12. The off-centered arrangement of the passage 18 and enclosed internal space 22 helps provide a greater agent loading capacity, among other things, without having to increase the outside diameter 34 of elongated member 12. FIG. 2A also further illustrates the manner in which opposing surfaces of inner wall portion 20 define portions of both passage 18 and enclosed internal space 22, respectively.

Although stent 10 of this embodiment, including elongated member 12, passage 18 and enclosed internal space 22 are all depicted as being of generally circular configuration, it should be readily apparent that alternative configurations could be used, such as, for example, elliptical, polygonal, wedge-shaped, or combinations thereof, some of which are shown in the following figures. It should be understood that the configurations of passage 18 and enclosed internal space 22, as well as the proximity of passage 18 relative to enclosed internal space 22, among other things, may be advantageously selected to modify properties of stent 10.

Figure 2B:
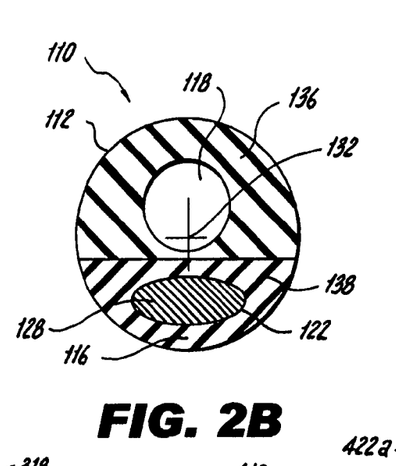
FIGS. 2B-2E are schematic transverse cross-sectional views of alternative configurations of stents constructed in accordance with the present invention.

FIGS. 2B-2E depict alternative cross-sectional views of other stents constructed in accordance with the present invention. FIG. 2B depicts a stent 110 with an enclosed internal space 122 having an elliptical cross-sectional shape and a passage 118 having a circular cross-sectional shape defined within elongated member 112. The passage 118 is positioned off-center from center axis 132 of elongated member 112, which alters the physical properties of stent 110.

For example, if imaging agent 128 is a liquid, the radial strength of the elongated member 112 may be reduced. It is believed that two factors may contribute to this reduction in radial strength. First, disposing the enclosed internal space 122 in an off-centered position gives rise to a thin outer wall portion 116 that structurally weakens the elongated member 112. Second, when radial pressure is applied to stent 110, the liquid within the enclosed internal space 122 may be unable to provide sufficient resistance to counter such radial pressure, resulting in the collapse of space 122. However, a reduced radial strength is often undesirable, as stents or stents are generally employed to maintain an open passage through a bodily lumen by resisting radial pressure exerted by adjacent tissue.

In contrast, if imaging agent 128 is a solid, the radial strength of elongated member 112 may be enhanced, because the solid within enclosed internal space 122 provides additional structural support to stent 110. However, the enhanced radial strength resulting from a solid agent 128 may cause stent 110 to become generally less flexible than if imaging agent 128 is a liquid, thus making stent 110 increasing the difficulty associated with inserting stent 110 into a patient's body.

To compensate for the change in physical properties of the stent 110 due to an off-centered configuration of passage 118 and/or space 122, elongated member 110 may include a first polymer 136 and a second polymer 138, wherein the polymers 136 and 138 differ in their respective degrees of hardness on the Shore A durometer scale. For example, first polymer 136 can have a durometer value range of about 80 to about 100, or preferably about 85 to about 95, and more preferably about 90 on a Shore A scale, while second polymer 138 may be relatively less hard and have a durometer value range of about 70 to about 90, or preferably about 78 to about 90, and more preferably about 86 on a Shore A scale. The relative hardness of polymers 136 and 138 may depend on the chemical state of the agent and desired property of the finished product.

If the imaging agent 128 in the enclosed internal space 122 is a liquid, a second polymer 138 having a greater hardness on the Shore A durometer than the first polymer 136 can be selected and used. Conversely, if the imaging agent 128 is a solid, the second polymer 138 can have a lower hardness on the Shore A durometer scale than first polymer 136. Polymers of different hardness values may be used for different portions of the stent, along the length of the stent, such as in FIG. 2B, or used for different axial segments of the stent, such as distal, proximal, and middle segments.

Figure 2C:
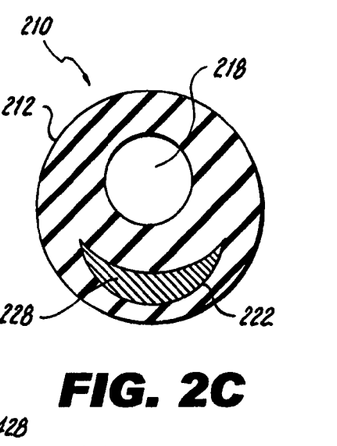

FIG. 2C depicts another alternative embodiment constructed in accordance with the present invention, wherein a stent 210 includes an elongated member 212 defining a cylindrical passage 218 and enclosed internal space 222 having a crescent-shaped cross sectional profile with an imaging agent 228 disposed therein.

Figure 2D:
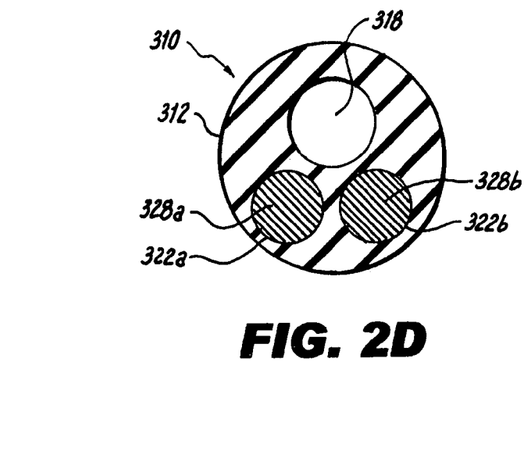

In another alternative embodiment, shown in FIG. 2D, a stent 310 includes an elongated member 312 that defines a generally cylindrical passage 318, a first generally cylindrical enclosed internal space 322a, and a second generally cylindrical enclosed internal space 322b. This embodiment may include a first imaging agent 328a and a second imaging agent 328b disposed within enclosed internal spaces 322a and 322b, respectively. Thus, stent 310 can be utilize multiple imaging agents, which may also be identical, to reference locations in a patient's body, among other things. Release of imaging agents 322a and 322b can be controlled temporally, such that imaging agents 322a and 322b can be delivered simultaneously or in succession to reference multiple locations within the patient. While enclosed internal spaces 322a and 322b are depicted herein as having circular cross sections, alternative configurations may be used, such as, for example, internal spaces having elliptical, polygonal, wedge-shaped cross sectional profiles, or combinations thereof.

Figure 2E:
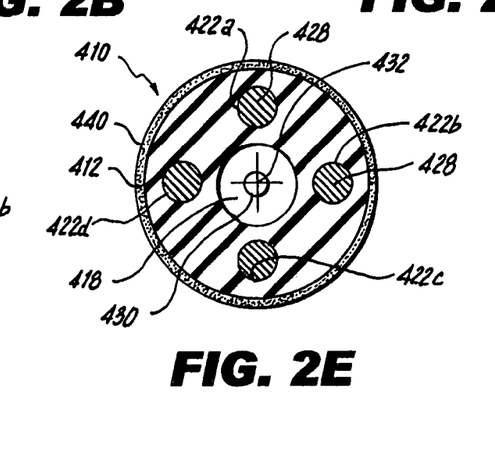

FIG. 2E depicts an alternative embodiment constructed in accordance with the present invention, wherein a stent 410 includes an elongated member 412 defining a passage 418 and a plurality of enclosed internal spaces, namely 422a, 422b, 422c and 422d, each containing imaging agent 428 disposed therein. Although enclosed internal spaces 422a-d of this embodiment are depicted as containing the same imaging agent 428 disposed therein, it should be readily apparent that enclosed internal spaces 422a-d may also contain different imaging agents in accordance with the present invention.

In this embodiment, center axis 430 of passage 418 is coaxial with center axis 432 of elongated member 412. Enclosed internal spaces 422a-d are disposed about passage 418 and may be spaced substantially equally apart from one another, as shown in FIG. 2E. Alternatively, two or more of enclosed internal spaces 422a-d may be disposed about passage 418 in a clustered or grouped arrangement, or arranged in two distinct groups on opposite sides of passage 418, wherein each group includes at least two enclosed internal spaces. While enclosed internal spaces 422a-d are shown in this embodiment as having substantially identical circular cross-sectional configurations, alternative configurations may be used, such as, for example, enclosed internal spaces 422a-d having elliptical, polygonal, wedge-shaped cross-sectional profiles or combinations thereof.

As illustrated in FIG. 2E, a biodegradable coating 440 can be disposed around elongated member 412 or any of the other embodiments constructed in accordance with the present invention. In operation, such a coating can be used to impart various characteristics to stent 410. For example, coating 440 can be a material which is biodegradable but also forms a distinct barrier to imaging agent 428 (or a barrier to one or more substances that may be included in enclosed internal spaces 422a-d with imaging agent 428), thus delaying the release and/or controlling the release rate thereof. Coating 440 may also include a substance providing a therapeutic benefit to the patient.

The dimensions of the various medical devices of the present invention may vary depending on the application and the size of the patient. For example, referring to FIG. 1A, an acceptable range for the outside diameter D1 of the elongated member 12 is about 4 French to about 9 French, and preferably about 4.8 French to about 7.3 French. When a larger outside diameter D1 is required, such as, for example, when a high flow volume or a greater stiffness is desired, an elongated member 12 having a larger outside diameter D1 may be used. An acceptable larger outside diameter D1 of the elongated member 12 may be about 8 French to about 12 French. The length of the elongated member 12 may also vary to suit a particular application, for example, the size of the patient and the particular bodily lumen that the device will be placed in.

A wide variety of polymer and agent combinations may be used to manufacture medical devices of the present invention. The medical device of the present invention may be constructed of a biocompatible plastic such as, but not limited to, any polyester, nylon based biocompatible polymers, polytetrafluoroethylene, silicone, polyurethane, polyethylene, and thermoplastics. In a particular embodiment, the medical device of the present invention is constructed from ethylene vinyl acetate (EVA).

A variety of methods can be used to manufacture a medical device according to the invention. For example, extrusion or injection molding can be used. During extrusion, a molten state polymer is forced under high pressure through an opening, thus forming a medical device in the shape of the opening's cross-section. Initially, the solid polymer is melted by rotation of a screw and barrel under extreme heat, friction, and pressure. After the resulting molten polymer is forced through a pre-shaped die of desired cross-section, the extrudate is cooled either through immersion within a water bath or by exposure to air.

The medical device may be constructed from more than one polymer having various characteristics and may be manufactured using co-extrusion techniques commonly known in the art. For example, polymers 136 and 138 of stent 110 of FIG. 2B may be hydrophobic and hydrophilic, respectively, thus controlling the diffusion profile of stent 110. During the co-extrusion process, the molten state polymers 136 and 138 are forced under pressure through an opening, simultaneously producing an elongated member 112 having heterogeneous physical and/or chemical properties.

Injection molding provides a similar mechanical method to manufacture the medical device of the present invention. During this process, an injection unit melts the polymer and subsequently injects the melt into a hollow mold cavity of desired shape. A ram-fed injection-molding machine contains a hydraulically operated plunger. The plunger spreads a thin layer polymer into a heated region, then converges the polymer melt at a nozzle, and lastly, injects the melt into the mold. Alternatively, a reciprocation screw injection molding machine utilizes a hydraulically operated rotating screw to melt, mix, and pump the polymer, after which, the screw serves as a plunger to inject the melt into the mold.

A stent in accordance with the present invention may be manufactured by extruding or injection molding the elongated member with a passage extending therethrough. Once the form is cooled, a laser drill may be used to bore the enclosed internal spaces and, if desired, pores to allow egress of the agent, or other substances included with the agent, from the enclosed internal spaces. It should be readily apparent that the inside diameters or dimensions, the number, and the arrangement of such pores can be varied to suit a particular application, for example, to control rate of flow or the location from where the agent, or constituents thereof. The pores can also be sealed with biodegradable plugs to delay the release of the agent or other substances included therewith.

Where the imaging agent is a liquid, a syringe may be used to inject the constituent directly into the enclosed internal space. Where the imaging agent is a solid, such as, for example, a powder, the imaging agent may be loaded into the enclosed internal space by gravity feeding or vacuum feeding.

In another embodiment, an imaging agent of the present invention is incorporated in a polymeric matrix of a medical device for placement within the body of a patient. Additional substances, such as substances that provide a therapeutic benefit, effect diffusion of the agent or other substances included therewith or the characteristics of the polymer in general may also be incorporated in the polymeric matrix along with the agent of the present invention. The polymeric matrix may also be configured to maintain the agent therein, or hold the agent while releasing other substances also contained in the polymeric matrix.

Medical devices according to the present invention can be formed (entirely or partially) of a polymeric matrix described above. Alternatively, a medical device designed for placement within the body of a patient can be partially or entirely coated with the polymeric matrix.

The polymeric matrix should be biocompatible with the patient's body and possess the ability to withstand conditions of the inner body environment. The polymer can, in fact, be biodegradable, but such degradation and release of the agent should be managed and controlled in such a way that it will give enough time for the patient to be fully diagnosed and treated accordingly before the material and the agent disintegrates, is bioresorbed or eliminated in the system. Moreover, the polymer should be chemically and physically compatible with both the agent and any other substances contained therein. In addition, the polymer, whether forming the medical device itself or being a coating on a medical device can be made to allow diffusion of body fluid, agent, and any other substances into and out of the matrix. The polymeric matrix can be either hydrophobic or hydrophilic, and typically is hydrophobic when the loaded matrix is a coating on a medical device.

In one embodiment, the polymeric matrix comprises primarily polymer macromolecules with naturally occurring spaces and voids interspersed throughout these macromolecules. These spaces naturally form a series of channels some of which may traverse from the matrix interior to the matrix surface. The total space that these voids encompass typically will be less than about 0.1 cubic centimeters per gram of polymer. The agent and any other substances can reside within these spaces. The permeability of the matrix to body fluid and certain particles, in combination with the internal spaces allow, in part, for the absorption of body fluid into the matrix and the release of an agent or substances therein out of the matrix. Upon absorption of body fluid, swelling may occur and new spaces may be created, thereby further affecting agent diffusion from the matrix. Other substances may be incorporated into the matrix to modify the rate of diffusion.

The polymeric matrix should be biocompatible with the patient's body. The polymer should possess the ability to withstand conditions of the inner body environment for the desired period of drug delivery. The polymer can, in fact, be biodegradable, but the degradation should not interfere with the desired course of drug release. Moreover, the polymer should be chemically and physically compatible with the agent and any other substances contained therewithin. In addition, the polymer, whether forming the medical device itself or being a coating on a medical device should allow diffusion of body fluid, agent, and any other substances included therewith into and out of the matrix. The polymeric matrix can be either hydrophobic or hydrophilic, and typically is hydrophobic when the loaded matrix is a coating on a medical device.

Various polymers possess the characteristics described above and, thus, are suitable for forming the matrix according to the invention. These polymers include, but are not limited to, acyl substituted cellulose acetates and alkyl derivatives thereof, partially and completely hydrolyzed alkylene-vinyl acetate copolymers, unplasticized polyvinyl chloride, crosslinked homo- and copolymers of polyvinyl acetate, crosslinked polyesters of acrylic and methacrylate, polyvinyl alkyl ethers, polyvinyl fluoride, silicone, polycarbonate, polyurethane, polyamide, polysulphones, styrene acrylonitrile copolymers, crosslinked poly(ethylene oxide), poly(alkylenes), poly(vinyl imidazole), poly(esters), poly(ethylene terephthalate), and chlorosulphonated polyolefines. In one embodiment the polymeric matrix comprises ethylene vinyl acetate (EVA), commercially available from DuPont as "Elvax 40W".

A biodegradable or otherwise erodable polymeric matrix according to the invention can be made of, for example, poly(lactide) co-glycolide and other polyesters, poly (ortho esters), polyanhydrides, polydioxanones, polyphosphazenes, polyhydroxybutyrate (PHB) and copolymers, polyhydroxyvalerate (PHV) and copolymers, acrylic polymers, polyamino acids, polyethylene glycol (PEG), polyethylene oxide (PEO), polylactic-glycolic acid and polyethylene glycol (PLGA-PEG) and other block or multiblock copolymers, polyvinyl acetate (PVA), and natural polymers like chitosan, alginate, dextran and other starch materials, and celluloses.

Figure 3A:
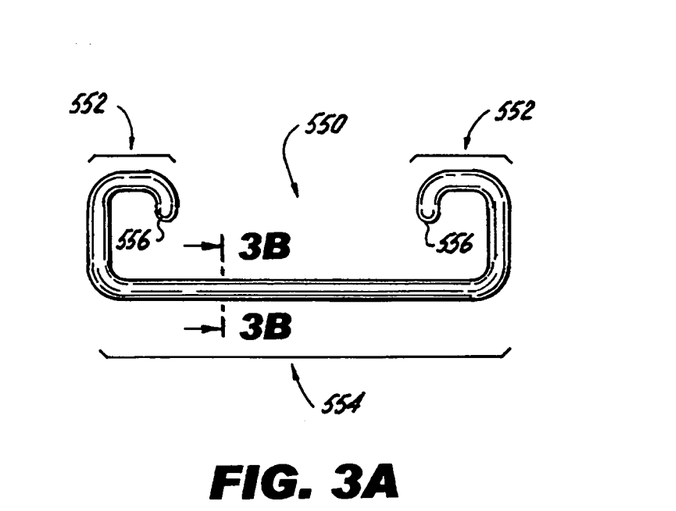
FIG. 3A is a schematic view of an exemplary medical device, specifically a ureteral stent constructed in accordance with another embodiment of the present invention.

Illustrative examples of medical devices constructed according to invention are described herein. FIG. 3A shows a ureteral stent 550 that includes two retention end portions 552, a central portion 554, and a lumen 556 extending through the length of the stent. A ureteral stent can be used for maintaining the patency of a patient's ureter to, for example, help drain urine from a kidney to the bladder in patients with ureteral obstruction or injury, or to protect the integrity of the ureter in a variety of medical procedures.

Figure 3B:
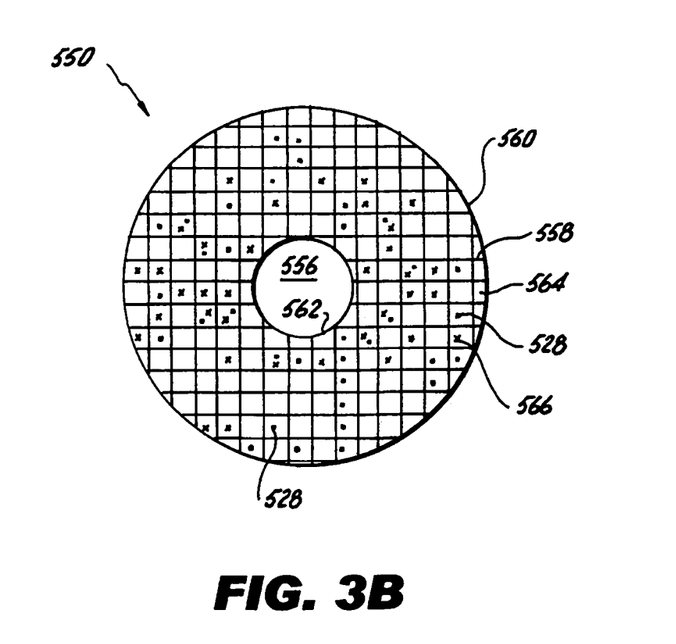
FIG. 3B is a cross-sectional view of the ureteral stent shown in FIG. 3A, taken along line 3B-3B of FIG. 3A, illustrating the macromolecular structure of a polymeric matrix loaded with one or more imaging agents according to the present invention.

FIG. 3B shows a cross-section of the ureteral stent 550 of FIG. 3A taken along line 3B-3B. The ureteral stent is formed of a polymeric matrix 558 fabricated in accordance with the present invention. An outer surface 560 of stent 550 is in contact with body fluids of the patient in which the device is placed (entirely or partially), and an inner surface 562 defining lumen 556. The polymeric matrix 558 comprises polymer macromolecules and defines spaces 564 between the polymer macromolecules. In this embodiment, many of these spaces contain at least an agent 528 and another substance 566, while others contain both agent 528 and material 566. It is contemplated that substance 566 can be a material which affects diffusion of agent 528 from matrix 558 when stent 550 is placed in the body of a patient or a substance which diffuses from stent 550 to provide a therapeutic benefit. It should be readily understood that polymeric matrix 558 can include agent 528 by itself, multiple agents, or additional substances in any medical device constructed in accordance with the present invention.

Figures 4A, 4B, 4C, 5A, 5B:
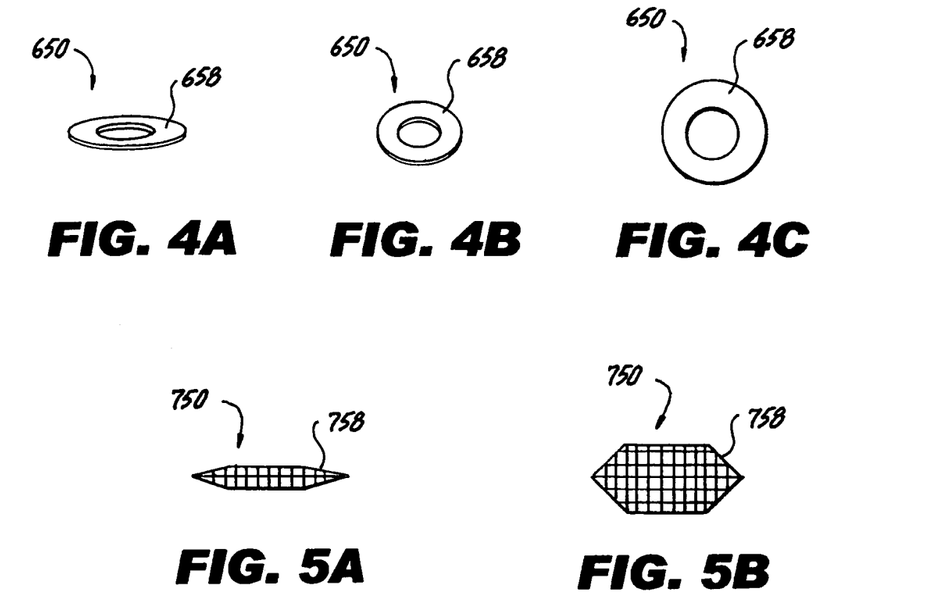
FIG. 4A is a schematic view of an expandable and compressible ring constructed from a polymeric matrix loaded with one or more imaging agents in accordance with the present invention, illustrating the ring in the compressed state.
FIG. 4B is a schematic view of the expandable and compressible ring shown in FIG. 4A, illustrating the expansion of the ring upon being released from a delivery device.
FIG. 4C is a schematic view of the expandable and compressible ring shown in FIG. 4A, illustrating the expansion of the ring in the hydrated state.
FIG. 5A is a schematic view of an expandable and compressible balloon constructed from a polymeric matrix loaded with an imaging agent in accordance with the present invention, the polymeric matrix being formed into a skeletal structure, illustrating the ring in the compressed state.
FIG. 5B is a schematic view of the expandable and compressible balloon of FIG. 5A, illustrating the expansion of the balloon in the hydrated state.
Figure 6:
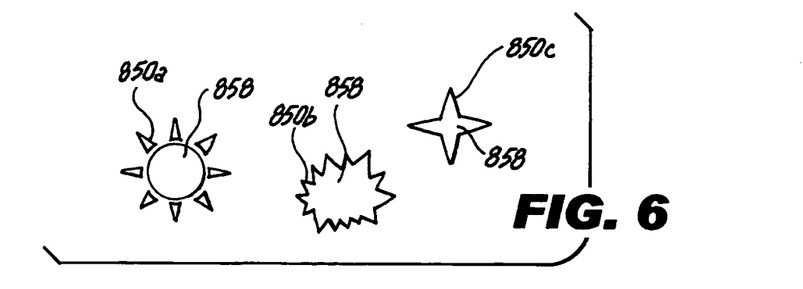
FIG. 6 is a schematic view of exemplary configurations of expandable and compressible tagging markers constructed of a polymeric matrix loaded with an imaging agent in accordance with the present invention.

FIGS. 4A-4C illustrate an expandable/compressible ring 650 formed of polymeric matrix 658 in accordance with the present invention. FIG. 5A-5B illustrates an expandable/compressible balloon 750 fabricated of a polymeric matrix 758 formed as a skeletal structure in accordance with the present invention. FIG. 6 illustrates exemplary expandable/compressible markers 850a, 850b and 850c fabricated of a polymer matrix 858 in accordance with the present invention. The expandable/compressible ring 650, balloon 750 and markers 850a, 850b and 850c are preferably biodegradable and can be delivered by a needle-like device while in the compressed state. As shown in FIG. 4B, ring 650 expands upon being introduced to the body of the patient and may expand further, as shown in FIG. 4C, as it absorbs body fluid. As shown in FIG. 5B, balloon 750 also expands upon being introduced to the body of the patient. Although not shown, polymer markers 850a, 850b and 850c react similarly, and in this embodiment, include protuberances or are otherwise configured to maintain in place within the body of a patient.

The aforementioned expandable/compressible medical devices preferably compress enough to allow them to be injected into the patient and expand sufficiently enough so that they resist being affected by tissue movement and do not dislodge from their intended position. Ring 650, balloon 750 and markers 850a, 850b and 850c can also be formulated from a polymer skeletal structure and include elastic coatings thereon. These devices can be formulated to adhere to tissue when hydrated.

Figure 7:
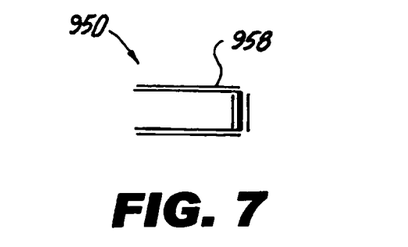
FIG. 7 illustrates a tissue clip constructed of a polymeric matrix loaded with an imaging agent in accordance with the present invention.

FIG. 7 illustrates a tissue clip 950 that is compounded/molded with a polymeric matrix 958 of the present invention. The clip 950 can be formed of biodegradable material. Clip 950 may also be formulated by coating a biodegradable material with a coating of the polymeric matrix loaded with an agent in accordance with the present invention.

Figure 8:
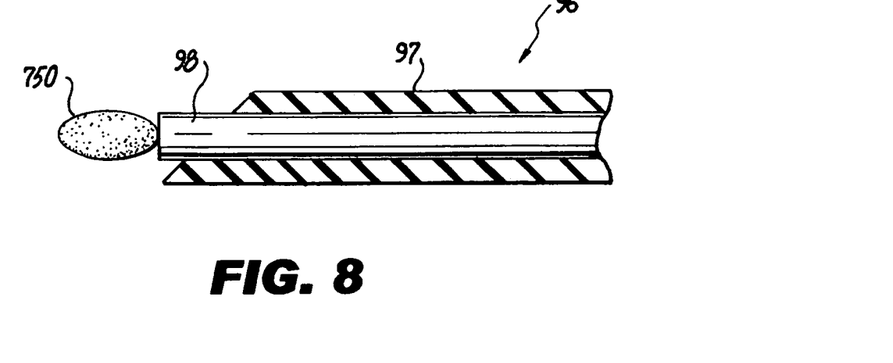
FIG. 8 is a schematic view of a needle device for delivering one or more medical devices of the present invention to a desired location in the body of a patient.
Figure 9:
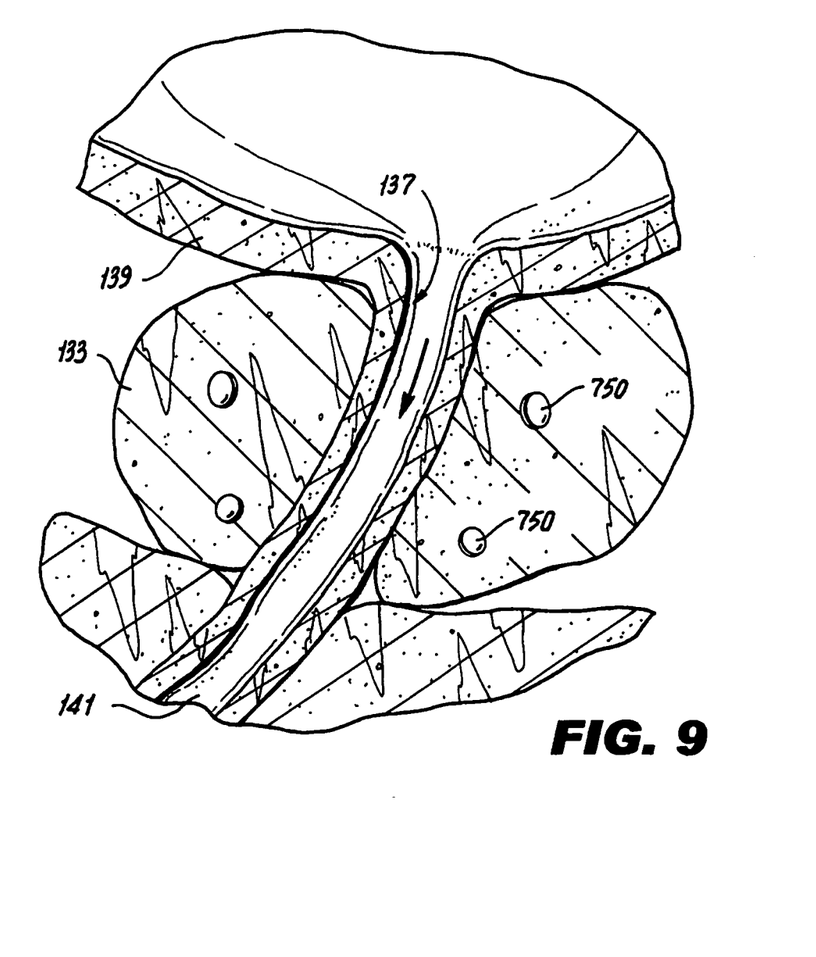
FIG. 9 illustrates some of the balloons of FIGS. 5A and 5B placed within the prostate in a patient's body.

FIG. 8 illustrates a needle device 96 including an outer hollow needle-like sheath 97 and an inner conduit 98 for introducing one or more medical devices constructed in accordance with the present invention, such as balloon 750, which is shown in FIG. 8 for illustrative purposes. The needle sheath 97 allows needle device 96 to be brought to a desired location in the body of the patient, such as a location where a biopsy was taken. Balloon 750 can then be delivered to the location through inner conduit 98. As shown in FIG. 9, balloons 750 can be delivered by a device, such as needle device 96, to various locations along the prostate 133 of a patient. A plurality of balloons 750 can be delivered to the body using needle device 96 during any one session. Other medical devices of the invention, such as ring 650 and markers 850a-c, can also be disposed in desired locations within the body of a patient using needle device 96.

A variety of methods can be used to manufacture a medical device or a coating according to this embodiment of the present invention. For example, extrusion or injection molding can be used. During extrusion, a molten state polymer is forced under high pressure through an opening, thus forming a medical device in the shape of the opening's cross-section. Initially, the solid polymer is melted by rotation of a screw and barrel under extreme heat, friction, and pressure. After the resulting molten polymer is forced through a pre-shaped die of desired cross-section, the extrudate is cooled either through immersion within a water bath or by exposure to air. Incorporation of the agent and any additional substances may occur prior to the extrusion process through precompounding with the polymer, or may occur as the polymer is melted during the actual extrusion process (Bridge, R., "Polymer Extrusion," URL: http://www.engr.uconn.edu/cheg/polymer/c256hnp.htm).

Injection molding provides a similar mechanical method to develop the medical device. During this process, an injection unit melts the polymer and subsequently injects the melt into a hollow mold cavity of desired shape. A ram fed injection molding machine contains a hydraulically operated plunger, first, to spread a thin layer polymer into a heated region; second, to converge the polymer melt at a nozzle; and lastly, to inject the melt into the mold. Alternatively, a reciprocation screw injection molding machine utilizes a hydraulically operated rotating screw to melt, mix and pump polymer after which, the screw serves as a plunger to inject the melt into the mold. The agent and any additional substances may be incorporated into the medical device by either precompounding both with the polymer, or alternatively, by addition during the melting process (Harris, L., "Injection Molding," URL: http://ww.engr.uconn.edu/cheg/polymer/injmold.htm).

In addition, various chemical processes can be used to manufacture the polymeric matrix. In a process known as imbibing, agent and any additional substances are incorporated into a preexisting polymeric matrix. The polymeric matrix is immersed in a solution of desired concentration of drug(s), desired concentration of material(s) and appropriate solvent. Toluene, dimethylformamide (DMF) and methyl ethyl ketone (MEK), among others, provide effective solvent for the imbibing process. Upon immersion, the matrix swells as the agent, any other substances to be included along with the agent and solvent penetrate into the matrix's network of channels and voids. Subsequently, solvent may be removed through ventilation, thereby entrapping the agent and any other substances included therewith within the matrix.

Solvent casting provides an alternative chemical method by which to manufacture the medical device. The desired amount of agent and any additional substances and matrix polymer are dissolved in an appropriate solvent, such as methylene chloride, to form a casting solution. The resulting mixture is then charged into a mold of desired shape. Finally, the mold is dried, usually under vacuum, allowing the matrix polymer to recrystallize and form the device with agent and any additional substances contained within the interpenetrating spaces.

Applying a polymeric matrix coating to a medical device can involve dipping or spraying. For example, a mixture of solvent, polymer, agent and any additional substances can be applied to the medical device by a dipping or spraying mechanism. Subsequently, the solvent carrier is evaporated forming a polymeric matrix coating containing the agent and any additional substances on the surface of the medical device.

Any of the embodiments of the present invention disclosed herein permit the placement of a marker or monitor at a particular location in or on a patient's body to allow later treatment or study to be done at that exact location. Having thus described various embodiments of the invention, various alterations, modifications, and improvements will be apparent to those of ordinary skill. Such alterations, modifications, and improvements are intended to be within the spirit and scope of the invention. The invention is not limited just to the foregoing description of various embodiments of the invention.

What is claimed is:

1. An imaging reference device comprising:
    an elongated body member having a center axis extending longitudinally through the member, the body member comprising a plurality of open, unplugged pores;
    an internal space defined within the body member, the internal space disposed substantially parallel to and off-center from the longitudinal center axis;
    a lumen defined by and extending through the body member, the lumen disposed substantially parallel to and off-center from the longitudinal center axis, the lumen separated from the internal space by an inner wall of the body member; and
    an imaging agent disposed within the internal space and released into a body of a patient by direct egress through the open, unplugged pores from the internal space, the imaging agent capable of being visualized from outside the body of the patient by use of an imaging system when the device is disposed within the body of the patient;
    wherein the body member is free from a lumen having a longitudinal axis extending along the longitudinal center axis.

2. The imaging reference device of claim 1 wherein the lumen allows for the passage of bodily fluids therethrough.

3. The imaging reference device of claim 1 wherein the internal space extends along substantially the entire length of the elongated member.

4. The imaging reference device of claim 1 further comprising at least two of the internal spaces.

5. The imaging reference device of claim 4 wherein each of the at least two of the internal spaces includes a different imaging agent disposed therein.

6. The imaging reference device of claim 1 wherein the imaging agent comprises a radio opaque material.

7. The imaging reference device of claim 1 wherein the imaging agent comprises a contrast agent.

8. The imaging reference device of claim 7 wherein the contrast agent comprises a negative contrast agent.

9. The imaging reference device of claim 7 wherein the contrast agent comprises a positive contrast agent.

10. The imaging reference device of claim 7 wherein the contrast agent includes gadolinium.

11. The imaging reference device of claim 1 wherein the imaging agent comprises iron oxide.

12. The imaging reference device of claim 7 wherein the contrast agent includes iron.

13. The imaging reference device of claim 1 wherein the imaging agent comprises a dye.

14. The imaging reference device of claim 1 wherein the imaging agent is capable of being visualized from outside the body of the patient by use of an MRI system, an ultrasound system, a PET system, a CT scan system, or an IR system when the device is disposed within the body of the patient.

15. The imaging reference device of claim 1 wherein the imaging agent is in the form of a powder, particulates, a liquid, a solid, a gel, macro bubbles, micro bubbles, a rod, or combinations thereof.

16. The imaging reference device of claim 1 wherein the internal space has a substantially circular cross sectional profile.

17. The imaging reference device of claim 1 wherein the elongated body member has a substantially circular cross sectional profile.

18. The imaging reference device of claim 1 wherein the internal space has a substantially elliptical cross sectional profile.

19. The imaging reference device of claim 2 wherein the lumen has a substantially circular cross sectional profile.

20. The imaging reference device of claim 7 wherein the contrast agent includes one or more substances having magnetic resonance.

21. The imaging reference device of claim 7 wherein the contrast agent includes one or more complexes of gadolinium.

* * * * *